(12) United States Patent
Rorvick et al.

(10) Patent No.: US 8,065,006 B2
(45) Date of Patent: Nov. 22, 2011

(54) ELECTROCHEMICAL CELL FOR IMPLANTABLE MEDICAL DEVICES

(75) Inventors: Anthony W. Rorvick, Champlin, MN (US); Kurt J. Casby, Grant, MN (US); David P. Haas, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1217 days.

(21) Appl. No.: 11/343,883

(22) Filed: Jan. 31, 2006

(65) Prior Publication Data

US 2006/0178708 A1 Aug. 10, 2006

Related U.S. Application Data

(63) Continuation-in-part of application No. 10/260,629, filed on Sep. 30, 2002, now abandoned.

(51) Int. Cl.
*A61N 1/375* (2006.01)
(52) U.S. Cl. ............................................. 607/36
(58) Field of Classification Search ............ 607/36
See application file for complete search history.

(56) References Cited

U.S. PATENT DOCUMENTS

| | | | |
|---|---|---|---|
| 4,987,519 A | 1/1991 | Hutchins et al. | |
| 5,103,818 A * | 4/1992 | Maston et al. | 607/9 |
| 5,456,698 A * | 10/1995 | Byland et al. | 607/36 |
| 5,458,997 A | 10/1995 | Crespi et al. | |
| 5,470,341 A | 11/1995 | Kuehn et al. | |
| 5,486,215 A | 1/1996 | Kelm et al. | |
| 5,549,717 A | 8/1996 | Takeuchi et al. | |
| 5,616,429 A | 4/1997 | Klementowski | |
| 5,926,362 A | 7/1999 | Muffoletto et al. | |
| 6,157,531 A | 12/2000 | Breyen et al. | |
| 6,459,566 B1 | 10/2002 | Casby et al. | |
| 6,498,951 B1 * | 12/2002 | Larson et al. | 607/36 |
| 6,613,474 B2 | 9/2003 | Frustaci et al. | |
| 6,819,544 B1 | 11/2004 | Nielsen et al. | |
| 2003/0027038 A1 | 2/2003 | Tsukamoto et al. | |
| 2003/0040779 A1 | 2/2003 | Engmark et al. | |
| 2004/0064163 A1 | 4/2004 | Aamodt et al. | |
| 2005/0002147 A1 | 1/2005 | Nielsen et al. | |
| 2005/0177193 A1 | 8/2005 | Nielsen et al. | |
| 2006/0178708 A1 * | 8/2006 | Rorvick et al. | 607/36 |

FOREIGN PATENT DOCUMENTS

DE  9109776 U1  10/1991
EP  0973211 A1  1/2000

* cited by examiner

*Primary Examiner* — Niketa Patel
*Assistant Examiner* — Alyssa M Alter

(57) ABSTRACT

An electrochemical cell for use in an implantable medical device is presented. The electrochemical cell includes a cover having a first surface and a second surface separated by an outer edge. The electrochemical cell also includes a case having a planar bottom, a side extending upwardly from the planar bottom, and an open top for receiving the cover.

27 Claims, 18 Drawing Sheets

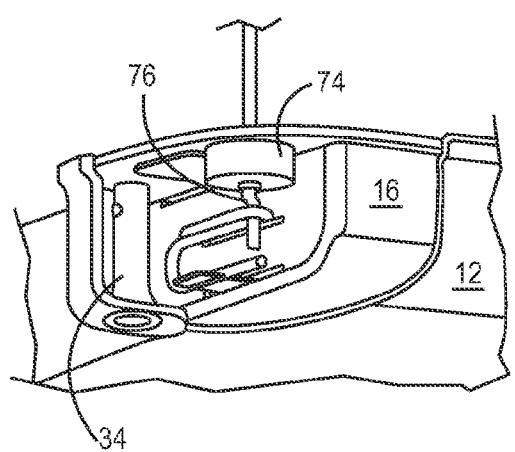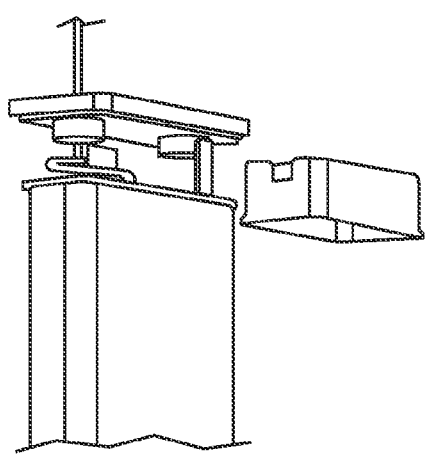
Fig. 12
Fig. 13
Prior Art

US 8,065,006 B2

ELECTROCHEMICAL CELL FOR IMPLANTABLE MEDICAL DEVICES

RELATED APPLICATION

This application is a continuation-in-part of U.S. patent application Ser. No. 10/260,629, filed Sep. 30, 2002 now abandoned, entitled "CONTOURED BATTERY FOR IMPLANTABLE MEDICAL DEVICES AND METHOD OF MANUFACTURE."

TECHNICAL FIELD

The invention relates generally to electrolytic cells for implantable medical devices, and, more particularly, to configurations for electrochemical cell encasements.

BACKGROUND

Implantable medical devices (IMDs) treat patients suffering from a variety of conditions. Examples of implantable medical devices are implantable pacemakers and implantable cardioverter-defibrillators (ICDs), which are electronic medical devices that monitor the electrical activity of the heart and provide electrical stimulation to one or more of the heart chambers, when necessary. For example, a pacemaker senses an arrhythmia, i.e., a disturbance in heart rhythm, and provides appropriate electrical stimulation pulses, at a controlled rate, to selected chambers of the heart in order to correct the arrhythmia and restore the proper heart rhythm.

IMDs are designed with shapes that are easily accepted by the patient's body while minimizing patient discomfort.

BRIEF DESCRIPTION OF THE DRAWINGS

FIG. 12 is a cutaway view of a headspace embodiment showing the feedthrough pin connection with the coupling.

FIG. 13 is an elevational, exploded pictorial view of the headspace in prior art implantable medical device batteries.

DETAILED DESCRIPTION

Figure 1:
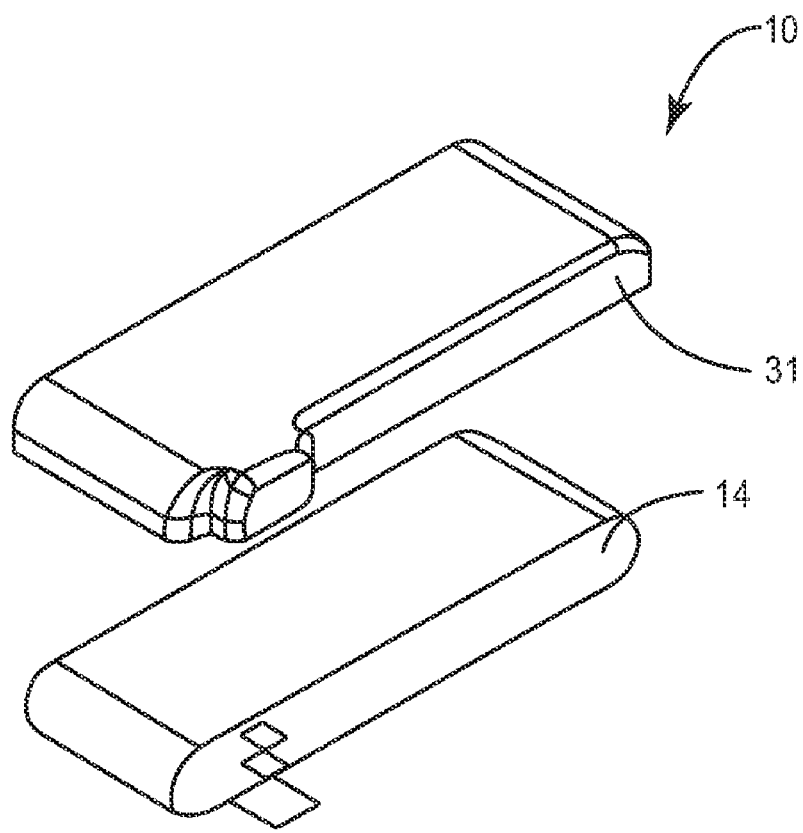
FIG. 1 is an exploded perspective view of a battery according to the present invention.
Figure 1:
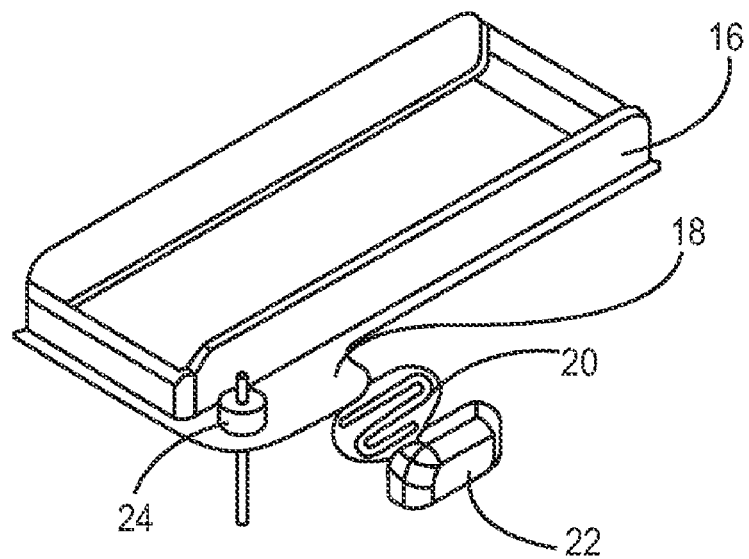

In the following description, references are made to illustrative embodiments for carrying out the invention. It is understood that other embodiments may be utilized without departing from the scope of the invention. The following detailed description is to be read with reference to the figures, in which like elements in different figures have like reference numerals. The figures, which are not necessarily to scale, depict selected embodiments and are not intended to limit the scope of the invention. Skilled artisans will recognize that the examples provided herein have many useful alternatives that fall within the scope of the invention.

Some embodiments of the present invention are particularly directed to high current batteries that charge capacitors with the desired amount of energy, (e.g. 20 joules to about 40 joules), in the desired amount of time, (e.g. less than 20 seconds).

Battery 10 includes a battery case 12 (FIG. 2), an electrode assembly 14, an insulator cup 16, a battery cover 18, a coupling 20, a headspace cover 22, a feedthrough assembly 24, and a battery case liner 31. Battery case 12 encloses the electrode assembly 14 and be hermetically sealed with battery cover 18.

Figure 2:
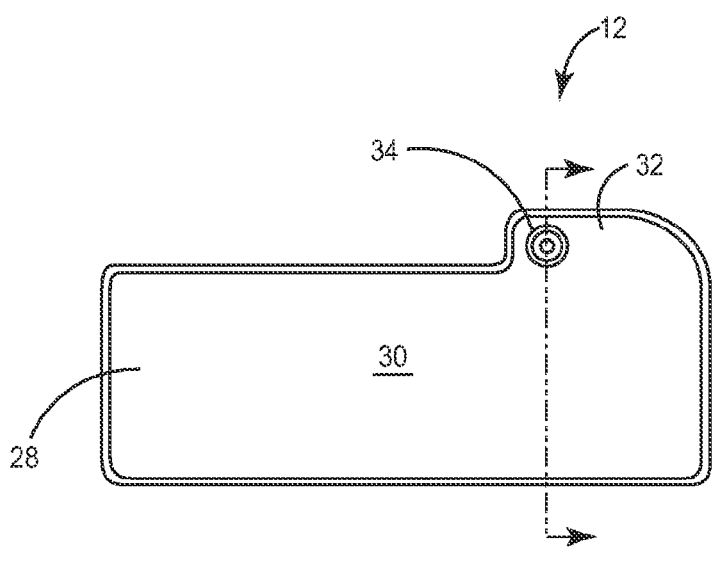
FIG. 2 is a bottom profile of a battery case embodiment of the present invention.
Figure 3:
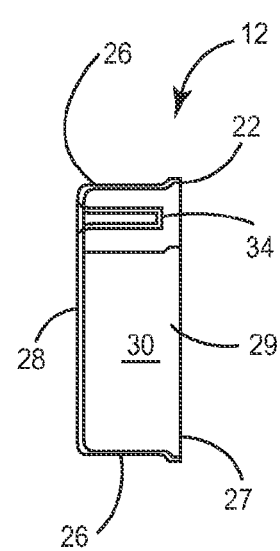
FIG. 3 is a side profile battery case embodiment of the present invention.

Referring to FIGS. 2 and 3, a bottom and side profile respectively is shown of a battery case. Battery case 12 is comprises battery space 30 which houses electrode assembly 14, headspace 32, fillport 34, which allows for the input of electrolyte into battery 10, and open end 29. Battery case 12 is generally arcuate in shape where sides 26 meet with top 28 of battery case 12. This construction accommodates the curved or arcuate ends of a coiled electrode assembly 14. The arcuate sides 26 can also nest within the arcuate edges of an implantable medical device (IMD) such as an implantable cardiac defibrillator.

Battery case 12 may comprise titanium, aluminum and stainless steel, resin-based materials, ceramic materials, fiber-impregnated materials, and the like. Further, it is contemplated that shallow battery case 12 could be manufactured from most any process including machining, stamping, casting, thermoforming, vacuum forming, milling, injection molding or so-called rapid prototyping techniques (e.g., using an SLA and the like). Headspace 32 houses insulators and connector tabs, which transfer electrical energy from electrode assembly 14 to the implantable medical device circuitry and will be discussed in more detail below. However, as shown in FIG. 2, a significant amount of headspace is reduced from prior battery assemblies such as the one shown in FIG. 13.

With reference again to FIG. 3, lip 27 is utilized to hold battery cover 18 in place not allowing cover 18 to drop within battery case 12. Further, lip 27 provides protection to electrode assembly 14 during the welding process, (e.g. laser welding) resistance welding, soldering, brazing with or without adhesive materials, thermoset compounds and the like. Lip 27 provides a shelf or ledge that prevents a laser beam from penetrating battery case 12. If this shelf were not there and a gap between cover 18 and case 12 were present electrode assembly 14 could be damaged by a laser penetrating the gap and potentially causing heat damage to electrode assembly 14.

Figure 4:
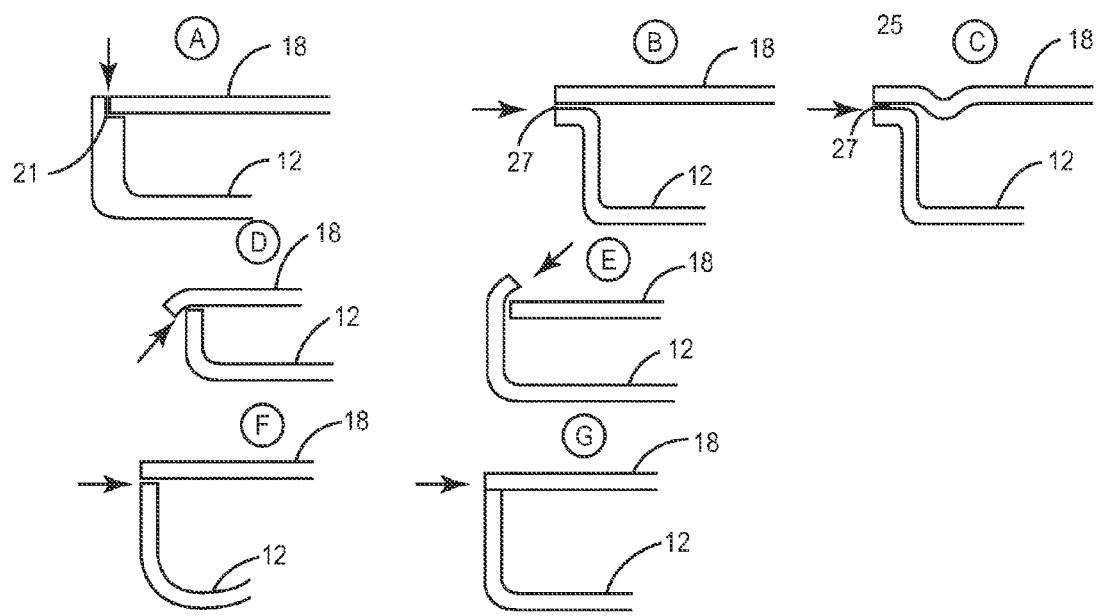
FIG. 4 is cutaway side profile of several attachment embodiments between a battery cover and a battery case.

With reference to FIG. 4, several cutaway side profiles of attachment embodiments between a battery cover and a battery case are shown. In profile A, lip 27 is cut at 90 degrees to provide even more protection during the welding process. While more protection is typically desired, the 90 degree lip 27 of profile A can be difficult to manufacture. In profile B, lip 27 is bent outward and then preferably cover 18 is placed overtop and butt welded to case 12. In profile C, lip 27 is also bent outward, however, in profile C, a crimp 25 is utilized to help prevent a laser beam from penetrating battery case 12. In profile D, lip 27 is eliminated and the outer edge of cover 18 is bent over before being welded to case 12 to help prevent the laser from penetrating case 12 during welding. In profile E, the outer edge of case 12 is bent over top of cover 18 before being welded. In profile F, cover 18 simple rests upon the upper edge of case 12 and then is butt welded together. In profile G, the upper edge of case 12 is bent slightly inward with cover 18 resting upon to be "butt" welded to case 12. Each of these embodiments provides protection to electrode assembly 14 during the welding process. Each embodiment prevents the welding laser beam (represented by the arrow in the Figure) from penetrating battery case 12 and damaging electrode assembly 14. Further, the term welding can encompass many types of attachment such as resistance welding and brazing. It is also contemplated that many types of attachment could be utilized without departing from the spirit of the invention.

As discussed above, traditional battery cases were deep cases wherein the opening to the case was perpendicular to the deepest portion of the battery. There are two limitations to this traditional design. First, there are manufacturing limitations to the amount of curvature, which can be implemented into the case. Therefore, most cases would have a substantially prismatic case, which, as discussed above, is limiting when packaging the case within the implantable medical device. Second, because the headspace exists at the open end of the case, it consumes an entire side of the case. In contrast to deep cases, battery case 12 is manufactured using a shallow form process, which allows for corners of case 12 to be radiused as well as providing for the possibility of many varying shapes of case 12. By doing so, the volume case 12 occupies is substantially reduced. Further, because battery case 12 can be manufactured with various shapes and contours, a substantial amount of headspace room can be eliminated and thus more volume within the implantable medical device can be reduced. The inventors of the present invention have found a reduction in excess of approximately about 10%.

Figure 5:
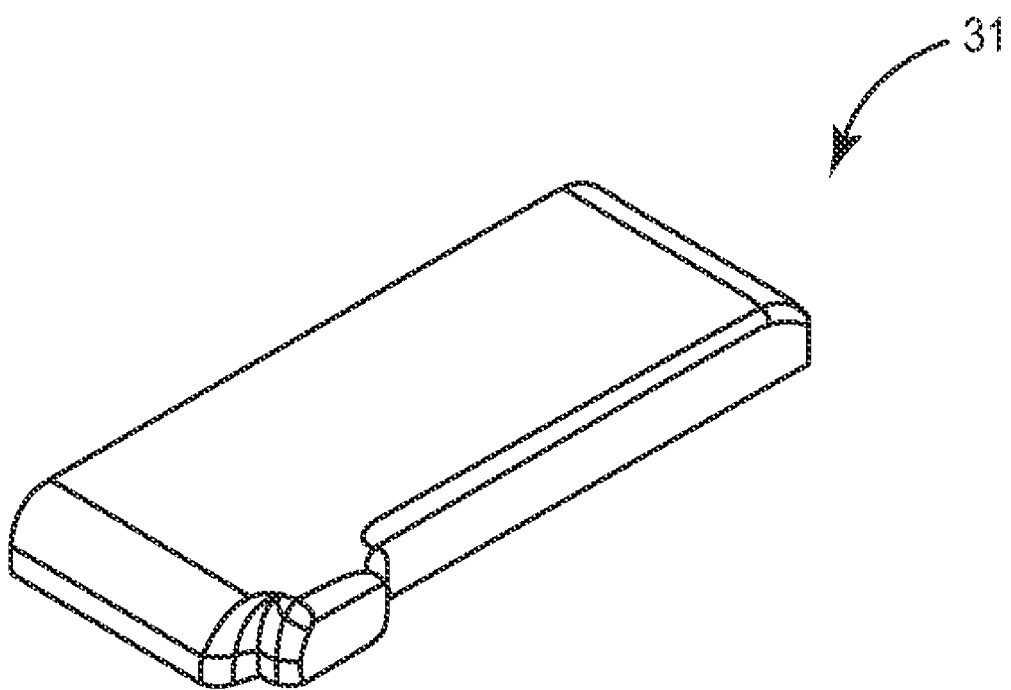
FIG. 5 is a side elevated perspective of a battery case liner of the present invention.

With reference to FIG. 5, a battery case liner used to isolate the battery case from the electrode assembly is shown. Case liner 31 comprises of ETFE and has a thickness of 0.013 cm. (0.004 inches), however, other thicknesses and types of materials are contemplated such as polypropylene, silicone rubber, polyurethane, fluoropolymers, and the like. Case liner 31 has substantially similar dimensions to battery case 12 except that case liner 31 would have slightly smaller dimensions so that it can rest inside of battery case 12. From the case liner's shape as shown in FIG. 5 and the battery case's shape as shown in FIG. 2, it is clear to one of skill in the art how case liner 31 would rest within battery case 12. For example, the headspace area of case liner 31 would line up with headspace 32 of battery case 12 except it would be slightly smaller to accommodate for fillport 34

Figure 6:
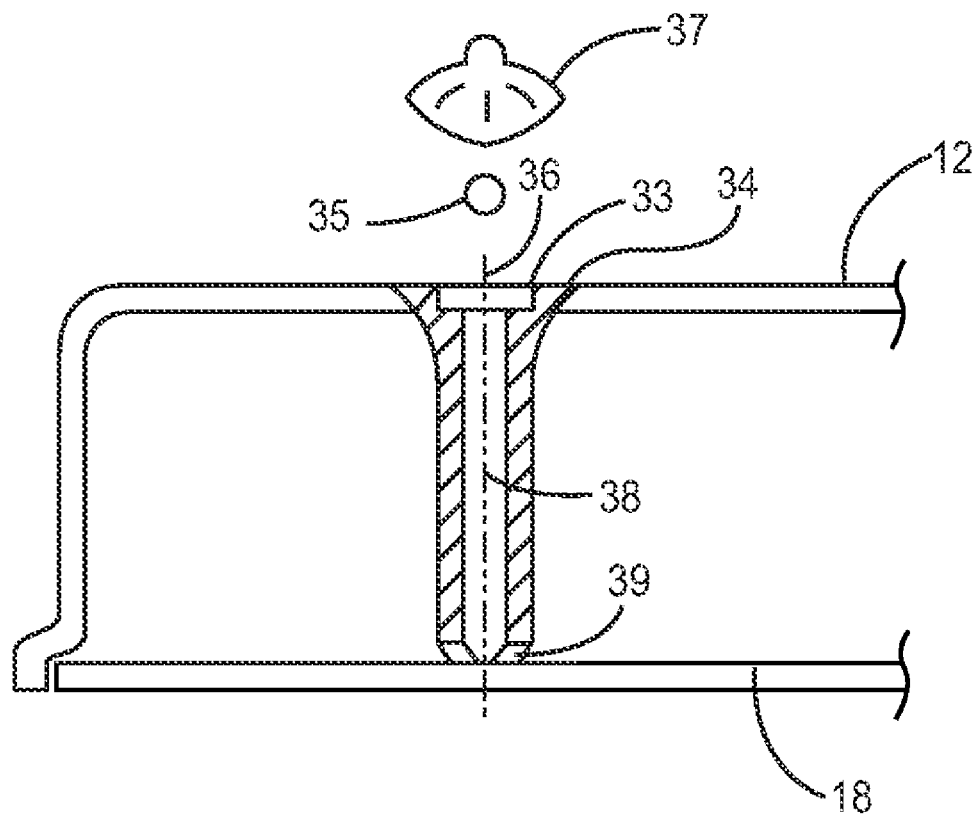
FIG. 6 is a front profile of an electrolyte fillport embodiment of the present invention.

With reference to FIG. 6, a front profile of the electrolyte fillport is shown with a fillport ball seal and a closing button. Fillport 34 routes electrolyte (e.g. lithium hexafluoroarsenate electrolyte) into battery 10. Fillport 34 is laser welded to battery case 12 and includes a hermetic seal to ensure no electrolyte leakage. However, it is contemplated that fillport 34 could be attached to case 12 in any fashion, such as any suitable hermetic joint. Fillport 34 comprises titanium and has a diameter of about 0.117 inches at the top and about 0.060 inches at the bottom. For ease of manufacturing and reliability of the weld, case 12 and fillport 34 are typically made from the same material.

From the figure it is shown that fillport 34 has an opening 36 in which to receive an electrolyte injection device that transfers electrolyte from the device to battery 10 through conduit 38. Further, it is shown that the upper portion of fillport 34 is tapered so that fillport 34 can rest within an opening in case 12 before fillport 34 is welded to case 12. Once the electrolyte has been injected within battery 10, fillport ball seal 35 is placed within conduit 38 to create a "press-fit" hermetic seal, which prevents any electrolyte from escaping through conduit 38. Closing button 37 is then placed over aperture 33 and is welded to fillport 34. Closing button 37 comprises medical grade titanium. Ball seal 35 comprises titanium alloy of titanium aluminum and vanadium, however, other materials and alloys are contemplated as long as they are electrochemically compatible. Fillport 34 is tapered from the top to the bottom. This provides for maximum space inside battery 10. Further the taper provides a larger upper area for button 37 to be welded to, which allows for button 37 to be larger and thus easier to handle and weld to fillport 34.

With further reference to FIG. 6, it is shown that fillport 34 extends entirely from case 12 to cover 18. Since case 12 and cover 18 are preferably 0.038 cm. (0.015 inches) thick, fillport 34 provides support by extending from case 12 to cover 18 so that an indentation or denting does not occur during the "press-fit" operation where ball seal 35 is pressed within conduit 38. If fillport 34 did not extend from case 12 to cover 18 there is a risk that denting could occur during the "press-fit" operation due to the thinness of case 12 and cover 18. Further, distal end 39 of fillport 34 is tapered so that electrolyte can freely enter battery 10. The taper allows conduit 38 to be unobstructed by cover 18 and thus the injection of electrolyte occurs more easily.

Figure 7:
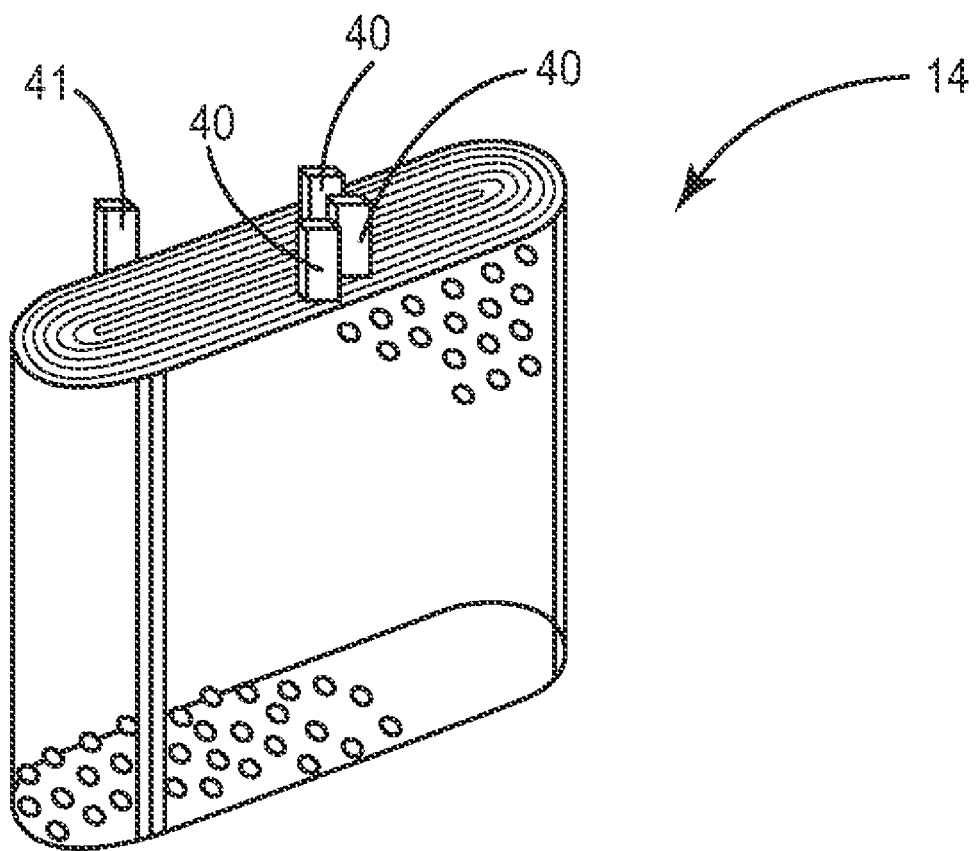
FIG. 7 is a side elevated perspective of an electrode assembly embodiment of the present invention.

Other fillport embodiments and locations are contemplated without departing from the spirit of the invention. One embodiment includes a low profile fillport (e.g., one that does not extend from the case to the cover) that is located near the corners of case 12 and cover 18. In this embodiment, indentation during the "press-fit" is inhibited by the support provided by the sides of case 12 in the corner. Further, this embodiment is implemented in case 12 or cover 18 as long as the low profile fillport is placed in a corner of battery 10. In another fillport embodiment, a filltube is located on case 12 or cover 18. After the electrolyte is injected into battery 10, the filltube is crimped shut and welded. This embodiment eliminates the "press-fit" operation. In another embodiment, a plug or button is welded over or into an open port where the electrolyte is injected. This embodiment eliminates a redundant seal. In yet another embodiment, a gasket seal or epoxy is utilized to plug an open port With reference to FIG. 7, the details regarding construction of electrode assembly 14, such as connector tabs, electrode pouches, etc., are secondary to the present invention and will be described generally below with a more complete discussion being found in, e.g., U.S. Pat. No. 5,458,997 (Crespi et al.). With reference to FIG. 7, electrode assembly 14 is a wound or coiled structure similar to those disclosed in, e.g., U.S. Pat. No. 5,486,215 (Kelm et al.) and U.S. Pat. No. 5,549,717 (Takeuchi et al.). However, electrode assembly 14 could be a folded or stacked electrode assembly structure. The composition of the electrode assemblies can vary, although one preferred electrode assembly includes a wound core of lithium/CSVO. Other battery chemistries are also anticipated, such as those described in U.S. Pat. No. 5,616,429 to Klementowski and U.S. Pat. No. 5,458,997 to Crespi et al., with the preferred cores comprising wound electrodes. Such a design provides a volumetrically efficient battery useful in many different implantable devices.

Electrode assembly 14 preferably includes an anode, a cathode, cathode connector tabs 40, anode connector tab 41, and a porous, electrically non-conductive separator material encapsulating either or both of the anode and cathode. These three components are wound to form electrode assembly 14. The anode portion of the electrode assembly can comprise a number of different materials including an anode active material located on an anode conductor element. Examples of suitable anode active materials include, but are not limited to: alkali metals, materials selected from Group IA of the Periodic Table of Elements, including lithium, sodium, potassium, etc., and their alloys and intermetallic compounds including, e.g., Li—Si, Li—B, and Li—Si—B alloys and intermetallic compounds, insertion or intercalation materials such as carbon, or tin-oxide. Examples of suitable materials for the anode conductor element include, but are not limited to: stainless steel, nickel, titanium, or aluminum. However, in one embodiment the anode is comprised of lithium with a titanium conductor The cathode portion of the electrode assembly preferably includes a cathode active material located on a cathode current collector that also conducts the flow of electrons between the cathode active material and the cathode terminals of electrode assembly 14. Examples of materials suitable for use as the cathode active material include, but are not limited to: a metal oxide, a mixed metal oxide, a metal sulfide or carbonaceous compounds, and combinations thereof. Suitable cathode active materials include silver vanadium oxide (SVO), copper vanadium oxide, combination silver vanadium oxide (CSVO), manganese dioxide, titanium disulfide, copper oxide, copper sulfide, iron sulfide, iron disulfide, carbon and fluorinated carbon, and mixtures thereof, including lithiated oxides of metals such as manganese, cobalt, and nickel. However, in a preferred embodiment the cathode is comprised of CSVO with a titanium conductor Preferably, the cathode active material comprises a mixed metal oxide formed by chemical addition, reaction or otherwise intimate contact or by thermal spray coating process of various metal sulfides, metal oxides or metal oxide/elemental metal combinations. The materials thereby produced contain metals and oxides of Groups IB, IIB, IIIB, IVB, VB, VIIB, VIIB, and VIII of the Periodic Table of Elements, which includes noble metals and/or their oxide compounds.

The cathode active materials can be provided in a binder material such as a fluoro-resin powder, preferably polytetrafluoroethylene (PTFE) powder that also includes another electrically conductive material such as graphite powder, acetylene black powder, and carbon black powder. In some cases, however, no binder or other conductive material is required for the cathode.

The separator material should electrically insulate the anode from the cathode. The material is preferably wettable by the cell electrolyte, sufficiently porous to allow the electrolyte to flow through the separator material, and maintain physical and chemical integrity within the cell during operation. Examples of suitable separator materials include, but are not limited to polyethylenetetrafluoroethylene, ceramics, non-woven glass, glass fiber material, polypropylene, and polyethylene.

Figure 8:
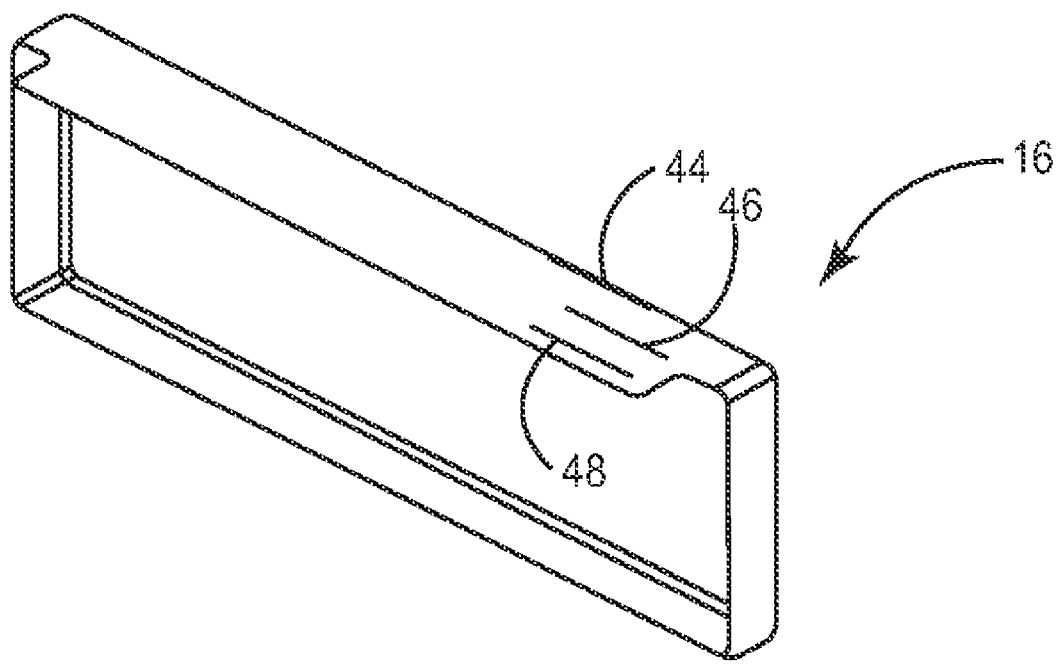
FIG. 8 is a side elevated perspective of an insulator cup embodiment of the present invention.
Figure 10:
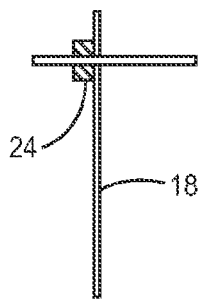
FIG. 10 is a side profile of a battery cover with a header assembly of the present invention.
Figure 9:
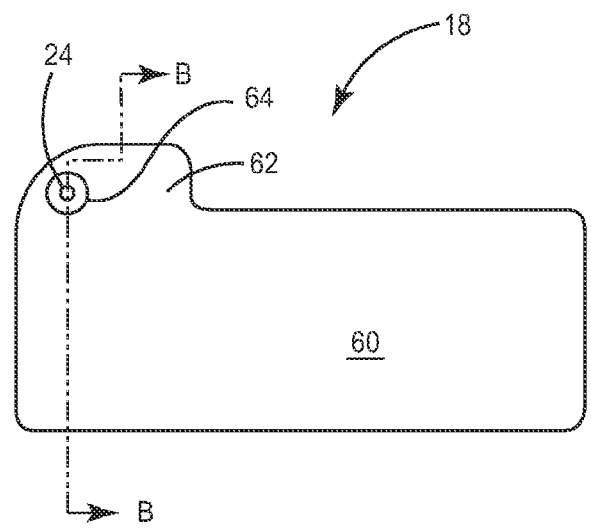
FIG. 9 is a top profile of a battery cover with a feedthrough assembly of the present invention.

Referring to FIG. 1, an insulator cup 16 electrically isolates electrode assembly 14 from battery cover 18. Referring to FIG. 8, an insulator cup 16 includes slits 44, 46, and 48 to accommodate connector tabs 40 and anode tab 41. Insulator cup 16 comprises ETFE with a thickness of 0.030 cm. (0.012 inches), however, it is contemplated that other thicknesses and materials could be used such as HDDE, polypropylene, polyurethane, fluoropolymers, and the like. Insulator cup 16 performs several functions including working in conjunction with battery case liner 31 to isolate battery case 12 and battery cover 18 from electrode assembly 14. It also provides mechanical stability for electrode assembly 14. In addition, it serves to hold the coil assembly together which substantially aids in the manufacturing of battery 10. Since electrode assembly 14 is preferably a wound coil, insulator cup 16 also prevents assembly 14 from unwinding. Insulator cup 16 further provides protection for assembly 14 during handling and during the life of assembly 14. Finally, cup 16 provides a thermal barrier between assembly 14 and cover 18 during the laser welding procedure that joins cover 18 with case 12, which is discussed in more detail below As stated above in detail, case 12 and cover 18 are preferably welded together to provide a hermetic enclosure for electrode assembly 14. However, due to the battery's structure, the weld is performed within 1 mm of electrode assembly 14. Since case 12 and cover 18 are first assembled before the welding process, a finite gap between case 12 and cover 18 typically exists. However, any time there is a finite gap there is the possibility that the laser beam utilized in the laser welding process may penetrate battery 10 and potentially damage electrode assembly 14. Therefore, molded insulator cup 16 may be comprised of ETFE and further is compounded or mixed with carbon black, although it may be coated with carbon black in lieu of the foregoing. The carbon coloring serves to make the insulator black. The black color serves to shield electrode assembly 14 from laser beam penetration into battery 10. Essentially cup 16 is opaque to the laser wavelength, which is approximately 1 micron. Alternatively, this thermal protection could be accomplished with a metal ring compatible with case 12 and cover 18, such as titanium, stainless steel, niobium, etc., however, cup 16 is an opaque polymer as discussed above FIGS. 9 and 10 depict a top and side profile of a battery cover 18. Battery cover 18 comprises an electrode assembly region 60, a headspace region 62, and a feedthrough aperture 64. Similar to battery case 12, battery cover 18 comprises titanium to provide a strong and reliable weld creating a hermetic seal with the battery case. However, it is contemplated that battery cover 18 could be made of any type of material as long as the material was electrochemically compatible. Battery cover 18 is designed to fit overtop the shallow opening 29 within lip 27 on the perimeter of opening 29. Therefore battery cover 18 rests on the small lip, substantially flush with the top of opening 29 which provides for substantial ease of manufacturing when battery cover 18 is laser welded to battery case 12

Figure 11:
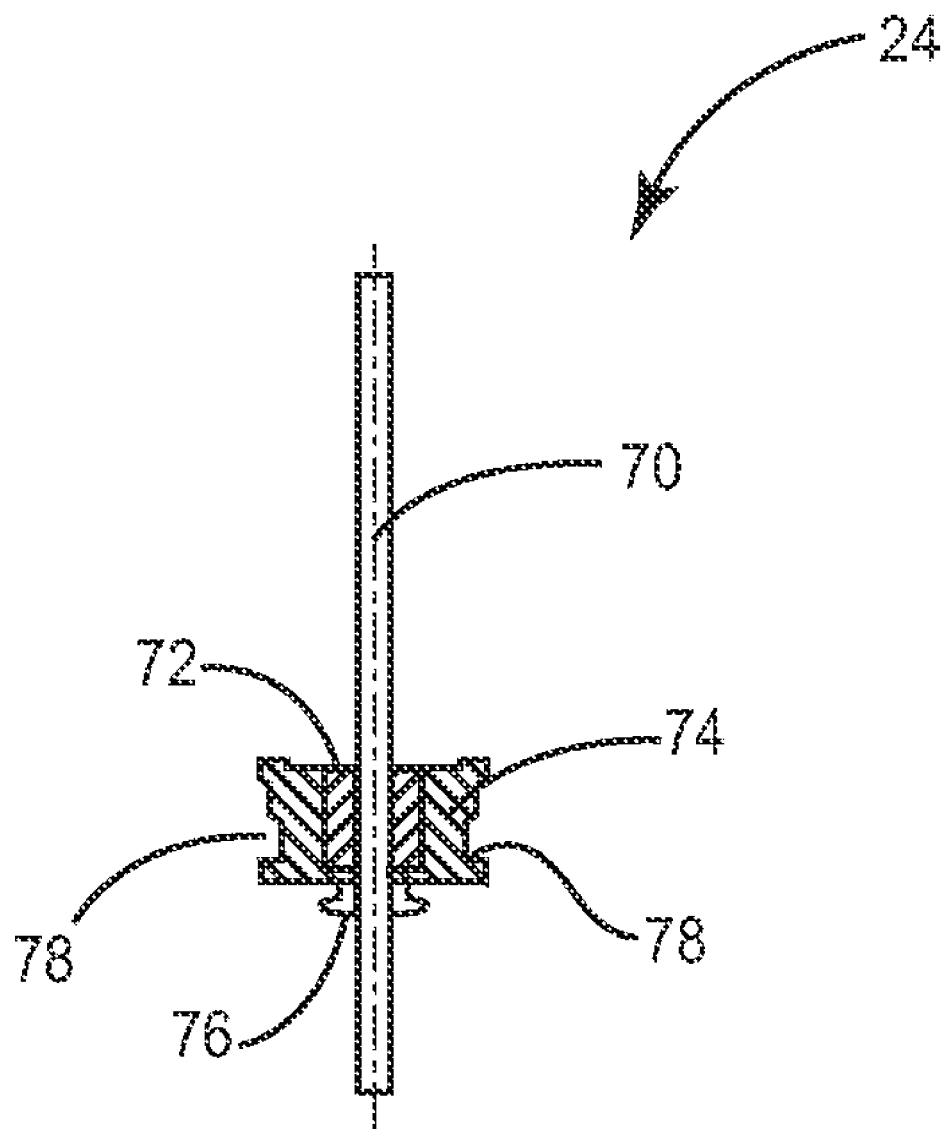
FIG. 11 is a front profile embodiment of a header assembly of the present invention.

Feedthrough aperture 64 is tapered outwardly not only to allow feedthrough assembly 24 to rest within aperture 64, but also to provide an isolation buffer between glass member 72 and the weld which will attach feedthrough assembly 24 to battery cover 18. With reference to FIG. 11, an embodiment for the feedthrough assembly is shown. Feedthrough assembly 24 is comprised of feedthrough pin 70, glass sealing member 72, ferrule 74, flange 76, and retention slots 78. As is shown in the figure, ferrule 74 is tapered at a substantially equal angle as the tapers on feedthrough aperture 64 so that it may be received within aperture 64. This tapered portion of ferrule 74 is also the location where the weld to join feedthrough assembly 24 to battery cover 18 occurs. The taper of ferrule 74 not only places the weld further from glass member 72, but also creates more surface area in which to dissipate the heat from the weld. As is discussed above, feedthrough aperture 64 and assembly 24 can be located anywhere on case 12 or cover 18

Feedthrough pin 70 may comprise niobium, however, any conductive material could be utilized without departing from the spirit of the invention. Niobium is chosen for its low resistivity, its material compatibility during welding with titanium, and its coefficient of expansion when heated. As will be discussed in more detail below, pin 70 may be welded to coupling 20 (FIG. 12) and to connector module 100 (FIG. 17) located outside of battery 10. Coupling 20 and contacts 114 and 116 on connector module 100 are preferably made of niobium and titanium respectively. Niobium and titanium are compatible metals. A strong reliable weld is created between compatible materials. Pin 70 has a diameter of 0.055 cm. (0.0216 inches), and may be selected for a high current application. Glass sealing member 72 is comprised of CABAL-12 (calcium-boro-aluminate) glass, which provides electrical isolation of feedthrough pin 70 from battery cover 18. The pin material is in part selected for its suitability in feedthrough assembly 24 for its ability to join with glass sealing member 72, which results in a hermetic seal.

CABAL-12 is very corrosion resistant as well as being a good insulator. Therefore, CABAL-12 provides for good insulation between pin 70 and battery cover 18 as well as being resistant to the corrosive effects of the electrolyte. Glass member 72 provides an electrical insulation resistance of 1000 mega ohms from pin 70 to ferrule 74 at 100 VDC per Mil-STD 202F method 302. Glass member 72 is then placed within a conduit on ferrule 74 having a diameter of 0.060 inches). Glass member 72 provides a hermetic seal both with pin 70 and ferrule 74 having a leak rate not exceeding 10.sup.-8 ATM STD cc/sec of helium per MIL-STD 202F method 112E. Ferrule 74 may be comprised of titanium that is annealed according to ASTM F67. Although, materials have been listed for the components listed above, it is contemplated that other materials could be utilized. Feedthrough pin 70, sealing member 72, and ferrule 74 are heated together to allow the glass to melt and reform to seal within ferrule 74 and around pin 70

After pin 70, glass member 72, and ferrule 74 are placed together the bottom of ferrule 74 may be overmolded where it is coated with polypropylene to provide electrical insulation between pin 70 and ferrule 74. The polypropylene overmold helps prevent pin 70 from being bent over to touch ferrule 74 thus creating an electrical short. The overmolding also provides mechanical short protection for other situations, such as pin 70 bending to bridge to connector tabs 40 and 41. Further, the polypropylene coating limits the amount of electrolyte exposure to glass member 72. It is contemplated that other insulation materials could be used as a coating such as PETFE (polyethylene tetra fluoro ethylene), ETFE (ethylene tetrfluorethylene), polyurethane, polyethylene, and the like. The polypropylene molding is held in place by retention slots 78, which act to prevent the molding from twisting off or pulling away from feedthrough assembly 24. Further, during the overmolding process flange 76 is created. Flange 76 provides a retention means for headspace insulator 22 (FIG. 14), which is discussed in more detail below. Flange 76 may include a thick plastic-thin plastic-thick plastic design, which allows for insulator 22 to be snapped onto flange 22.

In another embodiment, the overmolding is extended out over a plate with slots for cathode tabs 40. Tabs 40 are then welded to the plate, which in turn is welded to feedthrough pin 70. This embodiment provides a relatively rigid system prevents insulators from inadvertently folding or collapsing out of place.

With reference to FIG. 12, an embodiment showing the interconnection between a feedthrough pin and a coupling is shown. As is shown, coupling 20 is welded to cathode tabs 40 while anode tab 41 is in contact with battery cover 18. Coupling 20 is preferably comprised of niobium with a diameter of 0.055 cm. (0.0216 inches), which is compatible with pin 70. Coupling 20 is welded to feedthrough pin 70 to provide an electrical connection between the cathode of electrode assembly 14 and the implantable medical device. While for the purposes of this discussion coupling 20 is welded to cathode tabs 40 and feedthrough pin 70, it is contemplated that an alternate method of attachment may be utilized such as soldering, electrically conductive thermoset, electrically conductive glue and the like without departing from the spirit of the invention. Welding may provide the most reliable connection. Coupling 20 allows for ease in manufacturing by eliminating the need to bend tabs 40 or pin 70 to reach a coupling between them. Since coupling 20 has a "U" shape it allows for more compliance in aligning with the position of tabs 40 and pin 70. What is further shown with reference to FIG. 12 is that the headspace volume is substantially reduced when compared with prior implantable medical device batteries as shown in FIG. 13.

Figure 14:
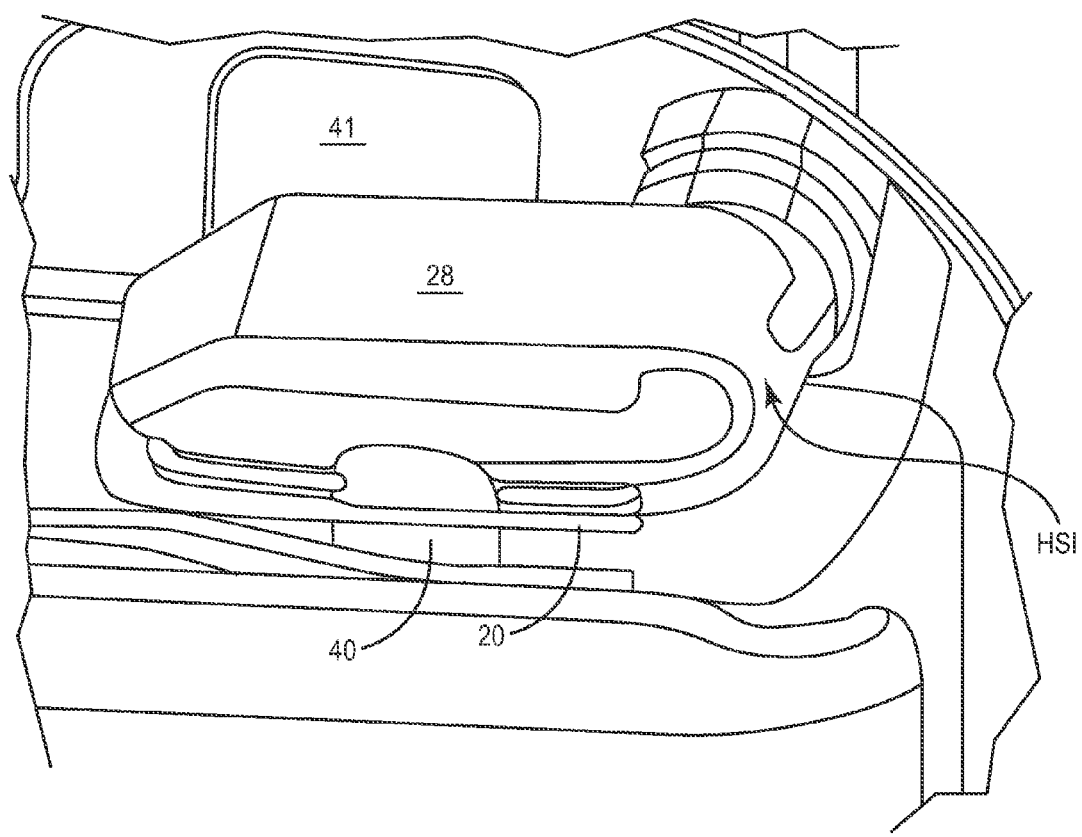
FIG. 14 is an elevated perspective of a headspace insulator embodiment of the present invention.
Figure 15:
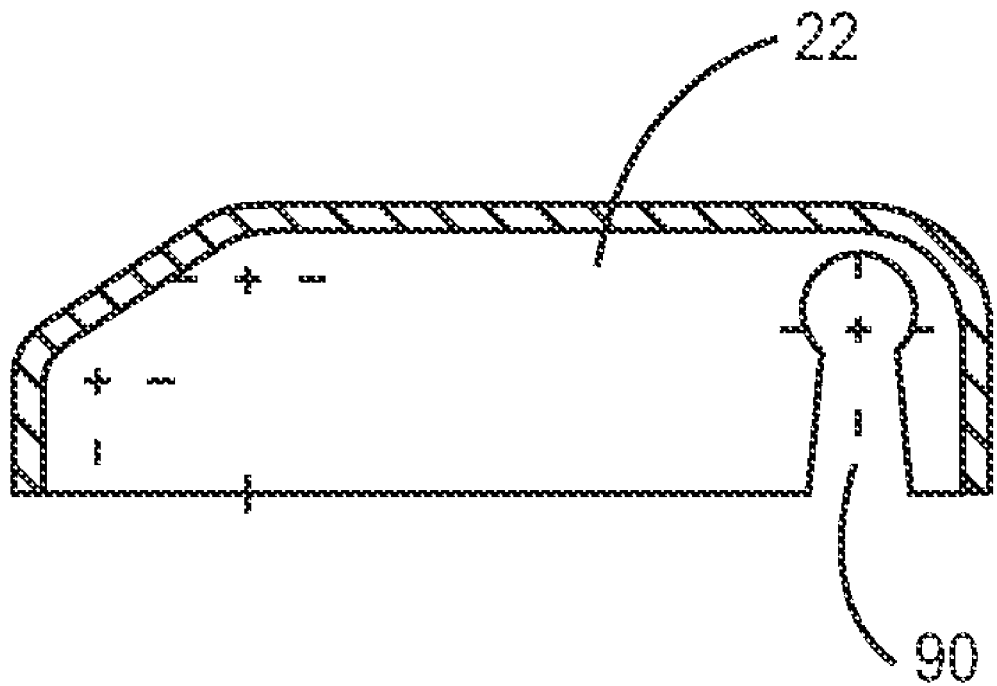
FIG. 15 is a rear profile perspective of a headspace insulator embodiment of the present invention.
Figure 16:
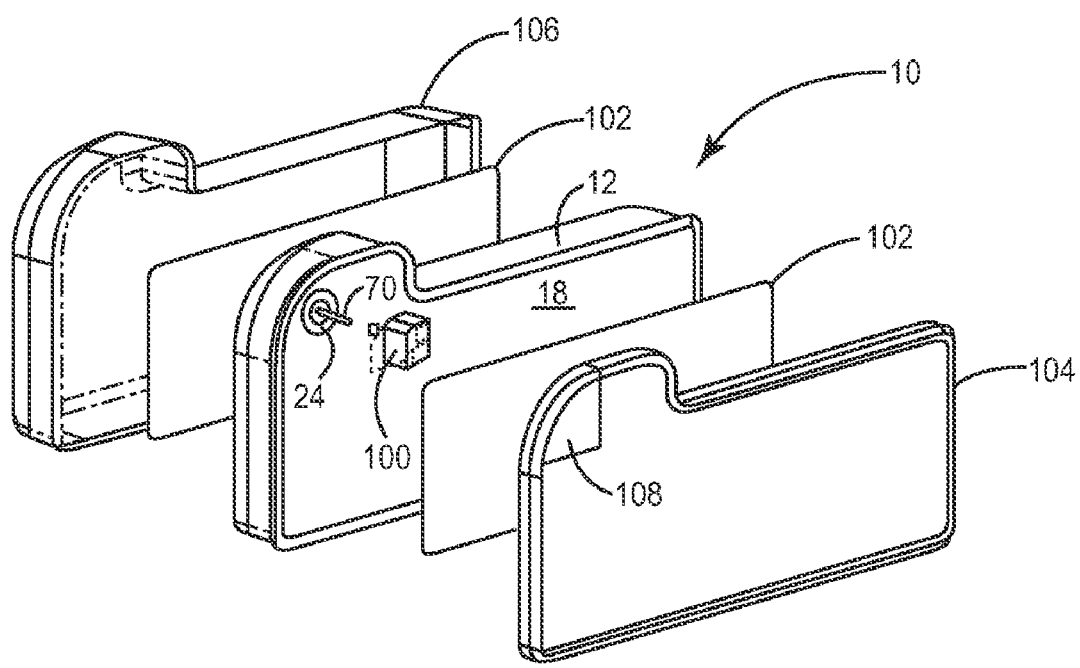
FIG. 16 is an exploded perspective view of battery insulators and connector.
Figure 17:
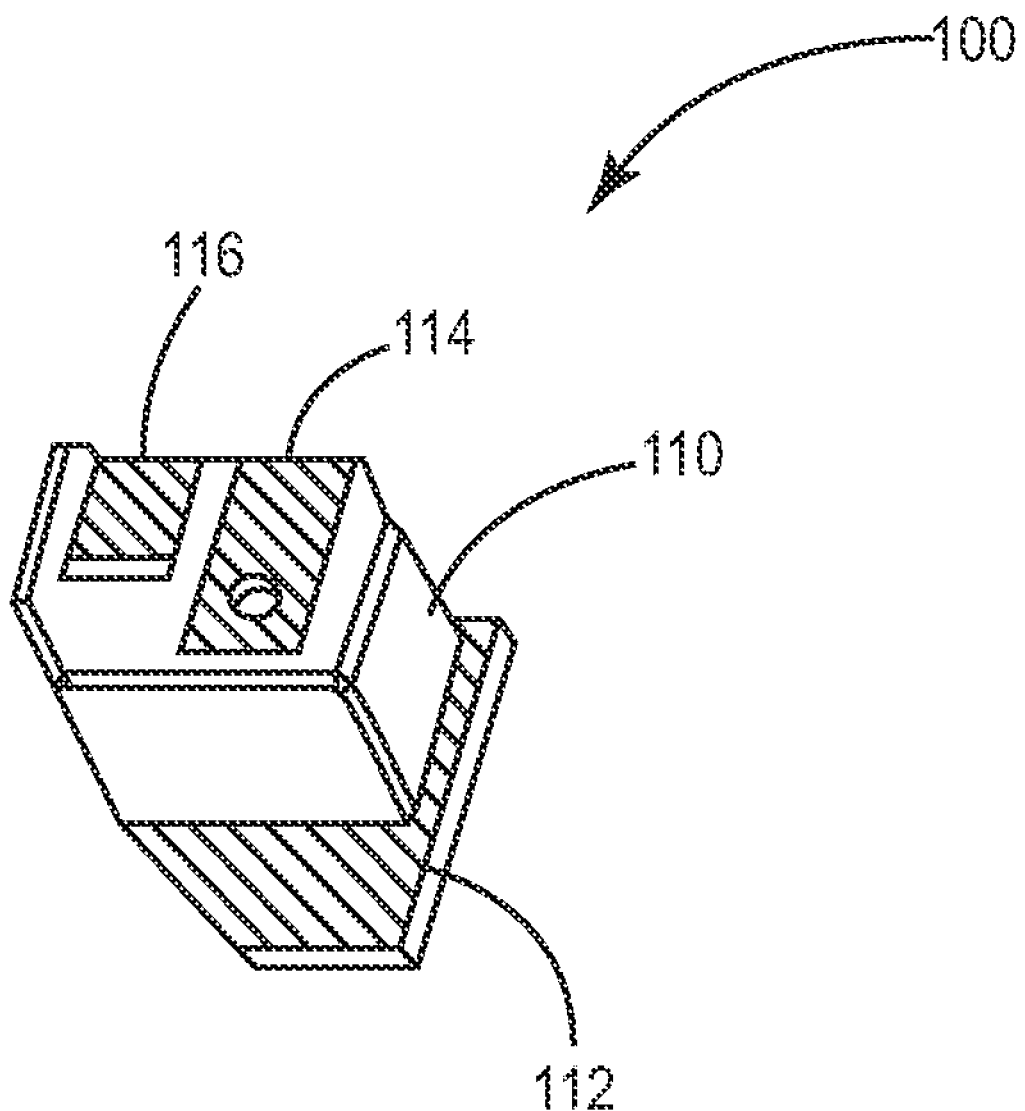
FIG. 17 is an elevated side profile of a battery connector embodiment of the present invention.

With respect to FIG. 14, a headspace insulator is shown. Headspace insulator 22 comprises polypropylene, however, other insulative materials are contemplated. Headspace insulator 22 may cover coupling 20 and cathode tabs 40. Headspace insulator 22 is designed to provide mechanical line of sight insulation and electrical protection from electrical shorts. Headspace insulator 22 also prevents any materials from contacting cathode tabs 40 and coupling 20, which could compromise the battery's operation. With reference to FIG. 15, which shows a rear profile view of the headspace insulation, slot 90 is shown, which snaps onto flange 76 of feedthrough assembly 24. This connection holds insulator 22 into place and protects cathode tabs 40 and coupling 20 during handling and discharge Referring to FIG. 16, a battery 10 being mechanically assembled as described in detail above, a battery connector 100 is connected to pin 70, which is described in more detail below. Connector 100 is utilized to route the energy from battery 10 to the implantable medical device. In an implantable cardioverter defibrillator the energy would be transferred to a switching system such as that described in U.S. Pat. No. 5,470,341 (Kuehn et al.). Battery insulators 104 and 106 are held in place on battery 10 with two pressure sensitive acrylic adhesive strips 102. These strips are similar to double back adhesive tape, which is tacky on both sides of the tape. While pressure sensitive acrylic is discussed for purposes of the embodiment, it is fully contemplated that other methods of attachment for insulators 104 and 106 could be utilized without departing from the spirit of the invention Insulators 104 and 106 are preferably comprised of a thermoplastic polyimide film, however, other insulator materials are contemplated. Insulators 104 and 106 provide electrical and mechanical insulation for battery 10. Since battery case 12 and cover 18 are negatively charged, they need to be electrically isolated from the rest of the implantable medical device. Further, insulators 104 and 106 provide mechanical insulation by protecting battery 10 during handling and thermal protection when the implantable device shields are welded together, which is outside the scope of the present invention With reference to FIG. 17, a battery connector 100 is shown. Battery connector 100 is comprised of a main body 110, a base 112, a positive contact 114, and a negative contact 116. Main body 110 provides a housing for base 112, positive contact 114, and negative contact 116 comprises of polyetherimide, however other insulator materials are contemplated. Body 110 also acts as an insulator to electrically isolate positive contact 114 from negative contact 116. Base 112, positive contact 114, and negative contact 116 comprise titanium, however other materials are contemplated. Battery connector 100 is placed over top of pin 70 in which pin 70 is received by an aperture in positive contact 114. Pin 70 is then preferably laser welded to positive contact 114 as well as base 112 which is laser welded to cover 18. What cannot be shown with reference to FIG. 17 is that negative contact 116 is in contact with base 112. Thus after the laser welding is complete there exists a positive charge on contact 114 and a negative charge on contact 116. Positive contact 114 and negative contact 116 are then ribbon bonded, as is known in the art, to the implantable medical device's circuitry. Connector 100 is the only exposed portion of battery 10 after it is received through triangular cut 108 as shown in FIG. 15. It is further noted that an alternative embodiment would include a negative charge on contact 114 and a positive charge on contact 116.

FIGS. 18-23 relate to weld joint embodiments that increase volumetric efficiency of an electrochemical cell.

Figure 18:
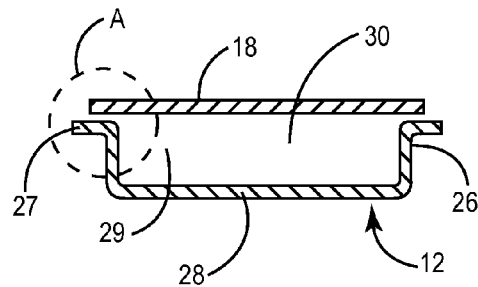
FIG. 18 is a cut-away side profile of one attachment embodiment of an electrochemical cell cover and case.

FIG. 18 is a cut-away side profile of one attachment embodiment between an electrochemical cell cover and case. Various embodiments presented herein for attaching a cover to an electrochemical cell case may improve volumetric efficiency, decrease manufacturing cost, shorten manufacturing time, lessen manufacturing difficulty and/or reduce the manufacturing failure rate fall-out. The various embodiments shown for attaching a cover to a case may be implemented in the manufacture of any electrochemical cell for use in an implantable medical device, including batteries and capacitors. Case 12 includes space 30 for housing internal cell components such as an electrode assembly as described above, a substantially planar bottom 28 and an upwardly extending side 26. Side 26 extends upward from planar bottom 28 terminating to form open top 29. Open top 29 is adapted to receive an electrode assembly and any other internal components to be enclosed in case 12.

After assembling internal cell components into case 12, cover 18 is placed over open top 29. Cover 18 is appropriately sized relative to case 12 such that a "step-like" junction is formed between a surface of cover 18 and a surface of side 26. The term "step-like junction," as used herein, refers to any junction in which two surfaces meet at an angle of 90 degrees or less to form an exposed step-like contour. The "step-like junction" referred to in contrast to a junction in which two surfaces meet to form a butt junction or two surfaces meet at an angle of 180 degrees, i.e. the two surfaces meet to form a flush surface. These types of junctions are illustrated in FIG. 19A through D for the sake of clarity.

In FIG. 19A, surface 1 and surface 2 meet at an angle of 90 degrees forming an exposed step-like contour as indicated by the dashed line. In FIG. 19B, surface 1 and surface 2 meet to form a butt joint. In FIG. 19C, surface 1 surface 2 meet at an angle of 180 degrees to form a flush surface as indicated by dashed line. It is contemplated that in some embodiments of the invention a step-like junction includes a junction formed when two surfaces meet at an acute angle as shown in FIG. 19D rather than a 90 degree angle as shown in FIG. 19A. In FIG. 19D, surface 1 and surface 2 meet at an angle less than 90 degrees but still form an exposed "step-like" contour as indicated by the dashed line.

Figure 20:
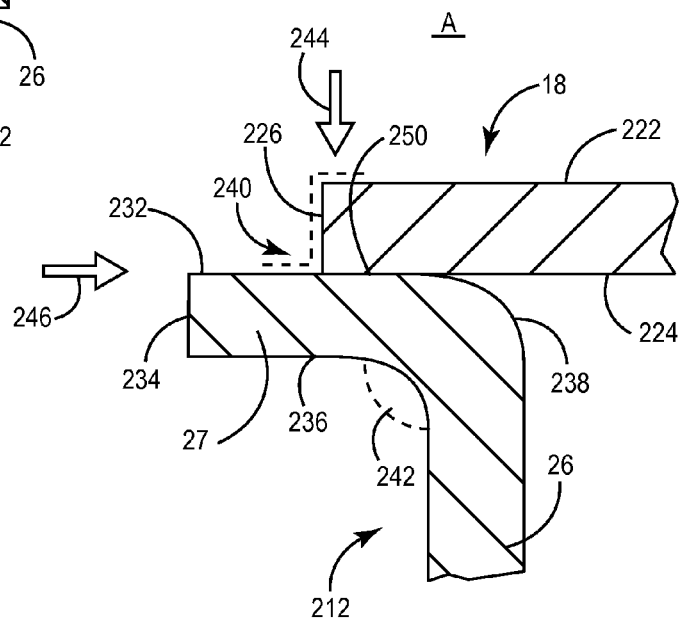
FIG. 20 is an enlarged view of a step-like junction formed by the case and cover profile shown in FIG. 18.
Figure 19:
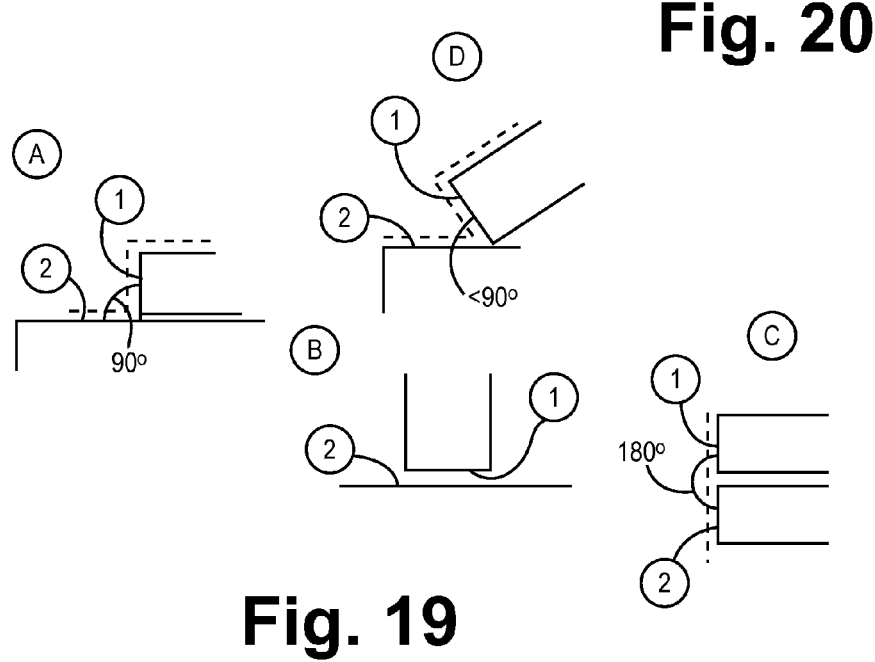
FIG. 19A through FIG. 19D illustrate a step-like junction in contrast to a butt junction and a flush junction.

FIG. 20 is an enlarged view of a step-like junction formed by the case and cover profile shown in FIG. 18. The enlarged view shown in FIG. 20 corresponds to the area A encircled by a dashed line in FIG. 18. Cover 18 includes an outer edge 226 disposed between an upper surface 222 and a lower surface 224. Side 26 is provided with a generally outwardly extending flange 27 or "lip." Flange 27 includes a flange outer edge 234 disposed between a flange upper surface 232 and a flange lower surface 236. Flange 27 extends outward at an angle 242 from side 26. In FIG. 20, angle 242 is approximately 90 degrees, however, in other embodiments angle 242 may be an obtuse angle such that flange 27 extends upward and outward from side 26. Inner corner 238 at the intersection of side 26 and flange 27 may be rounded to provide a smooth edge that is unlikely to cause damage to cell components as they are inserted into case 12.

Cover 18 is dimensioned to be larger than open top 29 of case 12 such that cover 18 rests on flange 27. Cover 18 is shown in FIGS. 18 and 20 to be smaller than the outer dimension of flange 27 such that cover outer edge 226 forms a step-like junction 240 with the flange upper surface 232. A welded joint 250 is formed at step-like junction 240 to seal cover 18 with case 12. Welded joint 250 may be formed using laser or galvanometer welding or any other fusion welding technique such as arc welding or plasma welding.

In one embodiment, welded joint 250 is formed using a top-down welding method wherein a welding beam is directed approximately perpendicular to the cover upper surface 222 and lower surface 224 down onto step-like junction 240, as generally indicated by arrow 244. In an alternative embodiment, welded joint 250 may be formed using a butt welding method wherein a welding beam is directed substantially parallel to cover lower surface 224, as generally indicated by arrow 246. An electrochemical cell encasement that includes a cover and case having the same outer dimensions, thereby forming a flush junction between the cover outer edge and the outer edge of the case side, is generally welded using a butt welding method as previously described in conjunction with FIG. 4. During butt welding, the laser should not penetrate through the space between the cover and the case and potentially cause damage to internal cell components. For example, precautionary measures may be taken such as including a weld ring within space 30 or providing a crimp in cover 18 as shown in FIG. 4, profile C.

Since both case and cover surfaces are exposed at step-like junction 240, the weld joint 250 can be formed relatively fast and/or using a relatively low welding energy applied from a top-down approach. Using a top-down approach reduces the likelihood of the welding beam from entering the encasement and damaging internal components since the weld beam is not directed toward the internal space 30. Weld joint 250 can be formed using relatively low laser energy or galvanometer welding resulting in controlled thermal input, which reduces the likelihood of damaging heat sensitive materials enclosed in case 12. The overall wall thickness of case 12 and cover 18 can thus be reduced since the weld joint 250 can be formed quickly, without excessive heating at step-like junction 240. As such the volumetric efficiency of the case 12 and cover 18 can be improved.

The weld joint distance away from internal cell components can be controlled by the size of flange 27 and relative size of cover 18. Step-like junction 240 can be located nearer flange outer edge 234 by increasing the outer dimensions of cover 18 such that cover outer edge 226 terminates more proximate to flange outer edge 234. The outward extension of flange 27 may be increased by increasing the size of flange 27 to thereby position step-like junction 240 even further from internal cell components. By positioning step-like junction 240 away from internal cell components, the potential risk of damaging internal cell components during a welding procedure is further reduced.

Figure 21A:
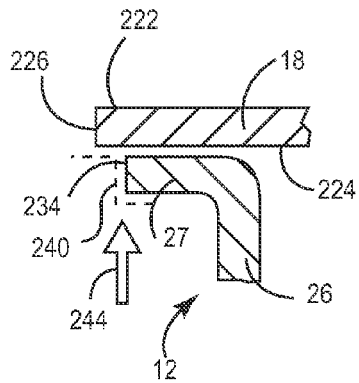
FIG. 21A through FIG. 21E are cut-away side profiles of alternative attachment embodiments of an electrochemical cell cover and case having an outwardly extending flange.

FIGS. 21A through 21E are cut-away side profiles of alternative attachment embodiments between an electrochemical cell cover and case having an outwardly extending flange. In FIG. 21A, cover 18 is sized with a larger outer dimension than the outer dimension of flange 27. As such, a step-like junction 240 is formed between cover lower surface 224 and flange outer edge 234. A weld beam can be applied in a top-down approach as illustrated by arrow 244. In the orientation shown, arrow 244 is pointing upward, however, the "top-down" approach refers generally to directing the weld beam normal or approximately normal to the surfaces to be joined by the weld joint. The "top-down" approach includes a weld beam directed at an angle to a surface being joined by the resulting weld joint. For, example a "top-down" weld beam may be directed toward step-like junction 240 at an angle is not limited to the normal approach illustrated by arrow 244.

This "top-down" approach can be contrasted with the butt welding approach as generally illustrated in the profiles of FIG. 4 wherein the weld beam is directed substantially parallel to the surfaces joined by the weld joint. The butt welding approach generally results in the weld beam being directed toward the internal space 30 of case 12 whereas the top-down approach generally results in the weld beam being directed away from internal space 30. It is appreciated that, in any of the cover and case attachment embodiments shown herein, a weld joint may be formed by either butt or top-down welding approaches.

Figure 21B:
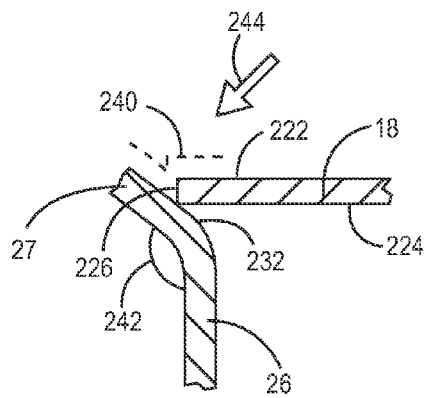

In FIG. 21B, flange 27 extends outward from side 26 at an obtuse angle 242. Step-like junction 240 is formed between flange upper surface 232 and cover outer edge 226. A weld joint may be formed at step-like junction 240 using a top-down approach as generally indicated by arrow 244.

Figure 21C:
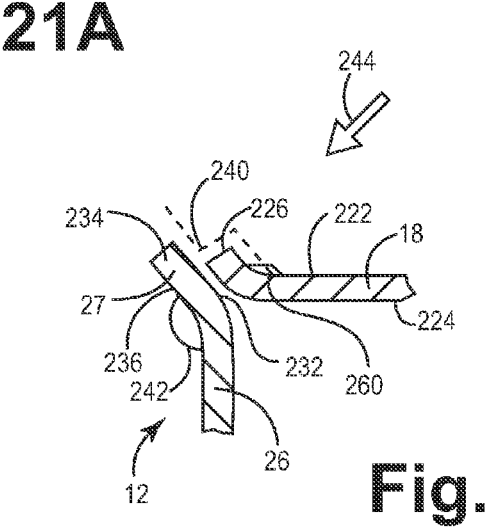

In FIG. 21C, flange 27 extends outward from side 26 at an obtuse angle 242. Cover 18 is provided with a preformed angle 260 corresponding to angle 242 such that cover lower surface 224 mates with flange upper surface 232. Pre-formed angle 260 promotes the self-registration of cover 18 with case 12 when cover 18 is placed over open top 29. Step-like junction 240 is formed between flange upper surface 232 and cover outer edge 226 and can be welded from a top-down approach as generally indicated by arrow 244. In other embodiments, cover 18 may be shaped with any self-registration feature matching a corresponding feature of case 12 to promote the alignment of cover 18 with case 12. For example, cover 18 may be shaped with a notch, step, groove or any other feature to promote alignment with a corresponding feature on case 12.

Figure 21D:
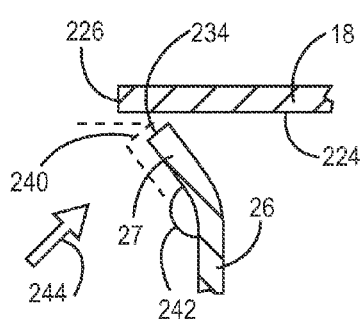

In FIG. 21D, flange 27 extends outward from side 26 at an obtuse angle 242. Cover 18 is sized larger than the outer dimension of flange 27 such that cover outer edge 226 extends outward from flange outer edge 234. A step-like junction 240 is formed between cover lower surface 224 and flange outer edge 234. A weld joint may be formed using a top-down approach as generally indicated by arrow 244.

Figure 21E:
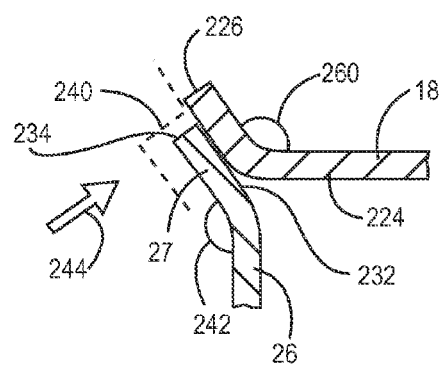

In FIG. 21E, flange 27 extends outward from side 26 at an obtuse angle 242. Cover 18 is provided with a preformed angle 260 corresponding to angle 242 such that cover lower surface 224 mates with flange upper surface 232. Cover 18 is sized with a larger outer dimension than the outer dimension of flange 27 such that cover outer edge 226 extends outward from flange outer edge 234. Step-like junction 240 is formed between flange outer edge 234 and cover lower surface 224. Step-like junction 240 can be welded from a top-down approach as generally indicated by arrow 244.

Figure 22A:
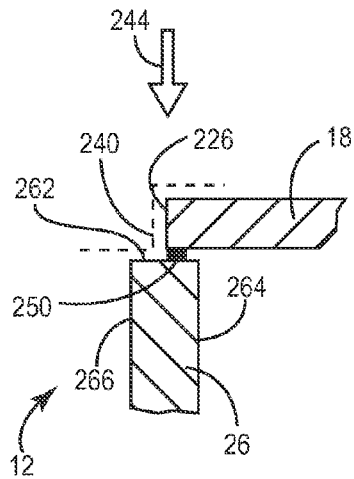
FIG. 22A through FIG. 22D are cut-away side profiles of alternative attachment embodiments of an electrochemical cell cover and case that include a step-like junction between a cover surface and a case surface.

FIGS. 22A through 22D are cut-away side profiles of alternative attachment embodiments between an electrochemical cell cover and case that include a step-like junction between a cover surface and a case surface. In FIG. 22A, side 26 has an upper edge 262 disposed between an inner side surface 264 and an outer side surface 266. Cover 18 is provided larger than the open top of case 12 but smaller than the outer dimension of case 12 such that cover outer edge 226 rests on side upper edge 262. A step-like junction 240 is formed by cover outer edge 226 and side upper edge 262. Step-like junction 240 can be welded using a top-down approach wherein a weld beam is directed as generally indicated by arrow 244 to from weld joint 250.

Figure 22B:
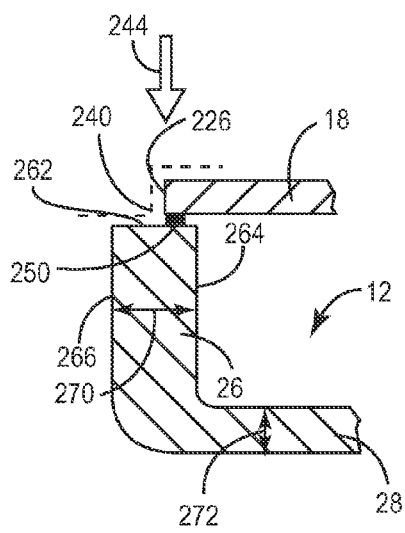

In FIG. 22B, case 12 is provided with at least two different wall thicknesses. Planar bottom 28 is provided with a wall thickness 272, and side 26 is provided with a greater wall thickness 270. By providing side 26 with a greater wall thickness 270, side upper edge 262 has a relatively greater surface area. A step-like junction 240 can be formed between side upper edge 262 and cover outer edge 226 with less stringent tolerances. Relatively thinner bottom 28 promotes volumetric efficiency of case 12. Weld joint 250 can be located further from internal cell components contained within case 12 by enlarging the side upper edge 262 and sizing cover 18 such that cover outer edge 226 is proximate side outer surface 266. Weld joint 250 can be formed using a top-down approach of the weld beam as indicated by arrow 244.

Figure 22C:
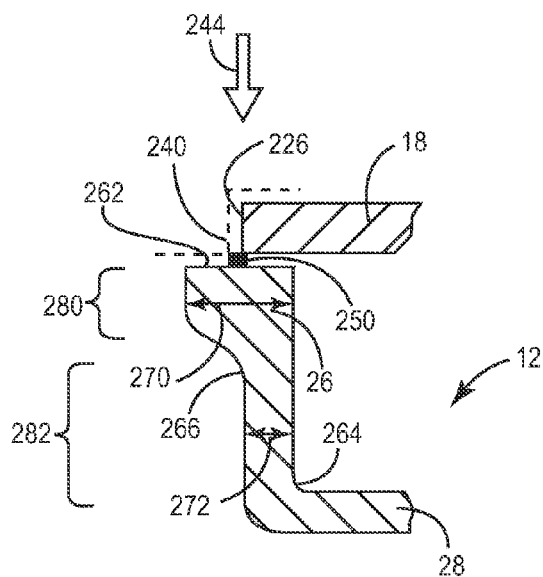

In FIG. 22C, case 12 is provided with at least two different side wall thicknesses. Side 26 is fabricated with a wall thickness 272 along a lower portion 282 of side 26, proximate planar bottom 28. Side 26 is fabricated with a relatively greater wall thickness 270 along an upper portion 280 of side 26, proximate side upper edge 262. Step-like junction 240 is formed by side upper edge 262 and cover outer edge 226. Weld joint 250 may be formed by directing a weld beam as generally indicated by arrow 244.

Figure 22D:
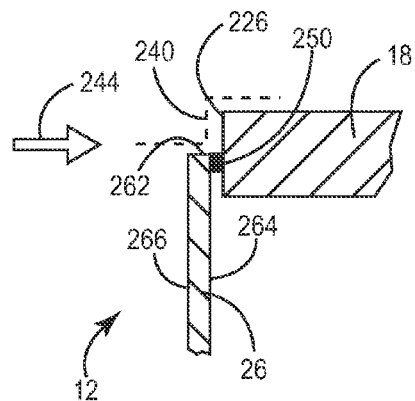

In FIG. 22D, cover 18 is sized such that cover 18 fits within open top of case 12. Cover 18 may rest on internal cell components or be press-fit within inner side surface 264. Step-like junction 240 is formed by cover outer edge 226 and side upper edge 262. A top-down approach for a weld beam in this embodiment is indicated by arrow 244 directed approximately normal to the surfaces to be joined by the weld joint. The location of weld joint 250 relative to cell components contained in case 12 may be controlled by the thickness of cover 18 and the height of side 26 relative to the thickness of cover 18. In any of the case and cover configurations described herein, the case and cover may be fabricated from any weldable material, including but not limited to, titanium, stainless steel, tantalum, or aluminum.

Figure 23A:
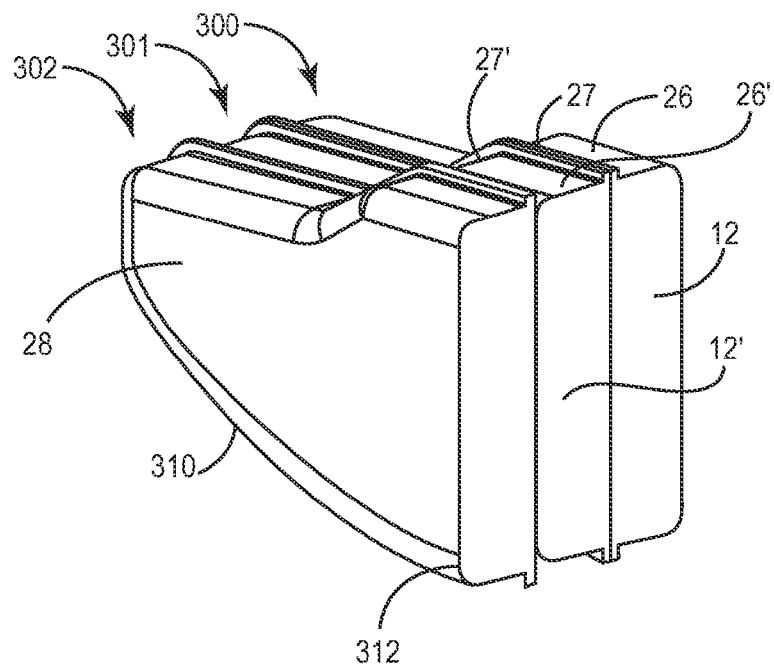
FIG. 23A and FIG. 23B are dimensional views of multiple electrochemical cells arranged for volumetrically efficient packaging.
Figure 23B:
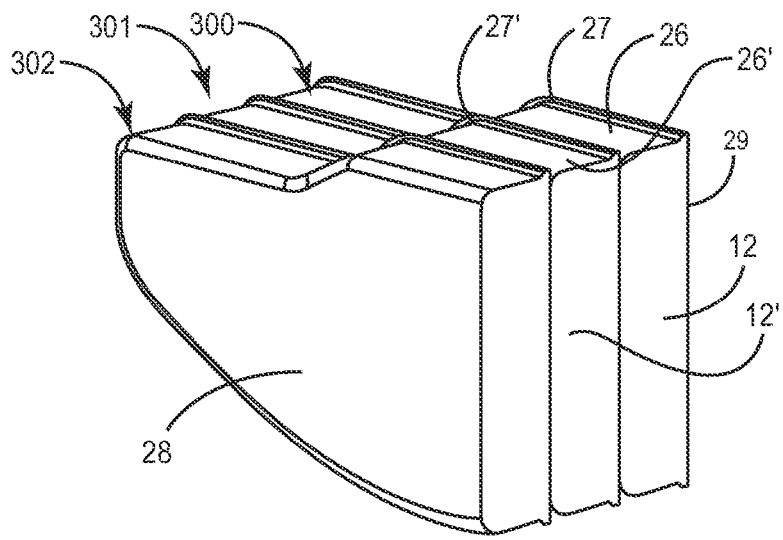

FIGS. 23A and 23B are dimensional views of multiple electrochemical cells arranged for volumetrically efficient packaging. In some embodiments, an implantable medical device may require multiple electrochemical cells, such as multiple high-voltage capacitors included in an ICD. In FIG. 23A, multiple cells 300, 301, and 302 are shown having a case and cover configuration corresponding to case 12 having a side 26 including a flange 27, as illustrated and described in conjunction with FIG. 18. Cell 300 and cell 301 are arranged in a "mirror image" packaging arrangement such that their covers are facing each other. Such a packaging arrangement promotes the translation of volumetric efficiency of the case and cover configuration to the device level in a device having multiple electrochemical cells.

The cells 300, 301 and 301 are further shown to have a contoured shape. As best seen in the view of cell 302, a contoured side 310, is provided and radiused at the intersection 312 where side 310 intersects with planar bottom 28.

In FIG. 23B, multiple electrochemical cells 300, 301 and 302 are shown having a case and cover configuration corresponding to case 12 having a side 26 including a flange 27 extending at an obtuse angle from side 26, as illustrated and described previously in conjunction with FIG. 21B, 21C or 21E. The outward and upward extension of flange 27 from wall 26 allows multiple cells to be nested in a cover-to-bottom arrangement. The nested arrangement prevents stack-up volume from reducing the overall volumetric efficiency of cells 300, 301 and 302.

The present invention has numerous applications. In particular, the present invention applies to all types of electrochemical cells. For example, electrochemical cell includes batteries (low current batteries, medium current batteries, high current batteries, etc.) and capacitors (e.g. high voltage capacitors).

The invention claimed is:

1. An electrochemical cell for use in an implantable medical device, comprising:
    a cover having a first surface and a second surface separated by an outer edge defining a plane;
    a case having a planar bottom, a side extending upwardly from the planar bottom, and an open top for receiving the cover;
    a step-like junction formed between the cover and the side when the cover is disposed over the open top, wherein either: a) the side of the case has an outwardly extending flange having a flange outer edge disposed between flange upper surface and flange lower surface, the flange outer edge defining a plane, and the plane defined by the outer edge of the cover and the plane defined by the flange outer edge are either parallel or intersect at a single point when the cover contacts the flange, or
    b) the side of the case has an upper edge disposed between an inner side surface and an outer side surface, the inner side surface and the outer side surface defining an inner side plane and an outer side plane and the plane defined by the outer edge of the cover and one of the planes defined by the inner and outer side surfaces of the side of the case are either parallel or intersect at a single point at an angle of less than 90°, wherein when the plane defined by the outer edge of the cover and one of the planes defined by the inner and outer side surfaces of the side of the case are parallel, the plane defined by the outer edge of the cover is between the planes defined by the inner and outer side surfaces of the case; and
    a welded joint formed at the step-like junction.

2. The cell of claim 1 wherein the side includes an upper edge disposed between an inner side surface and an outer side surface, and the step-like junction includes a junction formed between the side upper edge and the cover outer edge.

3. The cell of claim 2 wherein the case is provided with a first wall thickness corresponding to the planar bottom and a second wall thickness corresponding to the side, the second wall thickness being greater than the first wall thickness.

4. The cell of claim 2 wherein the side has a first wall thickness along a lower portion proximate the planar bottom and a second wall thickness along an upper portion adjacent the side upper edge, the second wall thickness being greater than the first wall thickness.

5. The cell of claim 1 wherein the side includes an upper edge disposed between an inner side surface and an outer side surface, and the step-like junction includes a junction formed between the inner side surface and the cover outer edge.

6. The cell of claim 1 wherein the side includes an outwardly extending flange having a flange outer edge disposed between a flange first surface and a flange second surface, and the step-like junction includes a junction formed between the cover outer edge and the flange first surface.

7. The cell of claim 6 wherein the flange upper surface includes a rounded corner at an intersection with the side inner surface.

8. The cell of claim 6 wherein the outwardly extending flange extends at an obtuse angle from the side.

9. The cell of claim 7 wherein the cover includes a preformed angle that causes the cover to mate with the outwardly extending flange when the cover is disposed over the case open top.

10. The cell of claim 6 wherein the cover outer edge extends outward from the outwardly extending flange, and the step-like junction includes a junction formed between the cover second surface and the flange outer edge.

11. The cell of claim 10 wherein the outwardly extending flange extends at an obtuse angle from the side.

12. The cell of claim 10 wherein the cover includes a preformed angle that causes the cover to mate with the outwardly extending flange when the cover is disposed over the case open top.

13. The cell of claim 1 wherein the cover is shaped to mate with the case side such that the cover self-registers when the cover is positioned over the case open top.

14. The cell of claim 1 wherein the weld joint includes a top-down welded joint.

15. The cell of claim 1 wherein the weld joint includes a laser welded joint.

16. The cell of claim 1 wherein the case side includes a radiused portion.

17. The device of claim 16 wherein the weld joint includes a top-down welded joint.

18. The device of claim 16 wherein the weld joint includes a laser welded joint.

19. The device of claim 16 wherein the case side includes a flange extending outwardly from the side.

20. The device of claim 19 wherein the step-like junction includes a junction formed between the cover and the flange.

21. The device of claim 20 wherein the case is arranged with a second case in a mirror-image arrangement.

22. The device of claim 20 wherein the case is arranged with a second case in a nested arrangement.

23. The cell of claim 1 wherein the case and the cover are formed from tantalum.

24. An implantable medical device, comprising:
    a case for enclosing an electrochemical cell having a planar bottom, a side extending upwardly from the planar bottom, and an open top;

a cover having a first surface and a second surface separated by an outer edge defining a plane disposed over the open top;

a step-like junction formed between the cover and the case wherein either: a) the side of the case has an outwardly extending flange having a flange outer edge disposed between flange upper surface and flange lower surface, the flange outer edge defining a plane, and the plane defined by the outer edge of the cover and the plane defined by the flange outer edge are either parallel or intersect at a single point when the cover contacts the flange, or b) the side of the case has an upper edge disposed between an inner side surface and an outer side surface, the inner side surface and the outer side surface defining an inner side plane and an outer side plane and the plane defined by the outer edge of the cover and one of the planes defined by the inner and outer side surfaces of the side of the case are either parallel or intersect at a single point at an angle of less than 90°, wherein when the plane defined by the outer edge of the cover and one of the planes defined by the inner and outer side surfaces of the side of the case are parallel, the plane defined by the outer edge of the cover is between the planes defined by the inner and outer side surfaces of the case; and a weld joint formed at the step-like junction.

25. An electrochemical cell for use in an implantable medical device, comprising:

a cover having an upper surface and a lower surface separated by an outer edge defining a plane;

a case formed of tantalum having a planar bottom, a side extending upwardly from the planar bottom having a side upper edge disposed between an inner side surface and an outer side surface, and an open top for receiving the cover, the cover being sized to rest on the side upper edge, the inner side surface and the outer side surface defining an inner side plane and an outer side plane and the plane defined by the outer edge of the cover and one of the planes defined by the inner and outer side surfaces of the side of the case are either parallel or intersect at a single point at an angle of less than 90°, wherein when the plane defined by the outer edge of the cover and one of the planes defined by the inner and outer side surfaces of the side of the case are parallel, the plane defined by the outer edge of the cover is between the planes defined by the inner and outer side surfaces of the case; and a welded joint formed between the cover lower surface and side upper edge.

26. The cell of claim 25 wherein the welded joint includes a top-down welded joint.

27. The cell of claim 25 wherein the cover is shaped to mate with the case side such that the cover self-registers when the cover is positioned over the case open top.

* * * * *